US012599309B2

(12) United States Patent (10) Patent No.: US 12,599,309 B2
Kremeier et al. (45) Date of Patent: Apr. 14, 2026

(54) METHOD AND DEVICE FOR DETERMINING VOLEMIC STATUS AND VASCULAR TONE

(71) Applicant: Loewenstein Medical Technology S.A., Luxembourg (LU)

(72) Inventors: Peter Kremeier, Karlsruhe (DE); Gerardo Tusman, Buenos Aires (AR)

(73) Assignee: CONSCIENTUS APS, Sakskøbing (DK)

( * ) Notice: Subject to any disclaimer, the term of this patent is extended or adjusted under 35 U.S.C. 154(b) by 306 days.

(21) Appl. No.: 17/995,596

(22) PCT Filed: Apr. 8, 2021

(86) PCT No.: PCT/EP2021/025131
§ 371 (c)(1),
(2) Date: Oct. 6, 2022

(87) PCT Pub. No.: WO2021/204426
PCT Pub. Date: Oct. 14, 2021

(65) Prior Publication Data
US 2023/0148884 A1 May 18, 2023

(30) Foreign Application Priority Data
Apr. 8, 2020 (DE) .......................... 102020002215.4

(51) Int. Cl.
*A61B 5/024* (2006.01)
*A61B 5/00* (2006.01)
(Continued)

(52) U.S. Cl.
CPC ...... *A61B 5/02416* (2013.01); *A61B 5/02007* (2013.01); *A61B 5/0295* (2013.01);
(Continued)

(58) Field of Classification Search
None
See application file for complete search history.

(56) References Cited

U.S. PATENT DOCUMENTS 9,782,090 B1 * 10/2017 Silverman .............. A61B 5/029
2006/0241506 A1 * 10/2006 Melker .............. A61B 5/14551
600/529
(Continued)

FOREIGN PATENT DOCUMENTS

WO WO-2006037184 A1 * 4/2006 ........... A61B 5/0826

OTHER PUBLICATIONS

Tusman Gerardo et al. "Photoplethysmographic characterization of vascular tone mediated changes in arterial pressure: an observational study" Journal of Clinical Monitoring and Computing, Springer Netherlands, NL, vol. 33, No. 5, Dec. 15, 2018 (Dec. 15, 2018), pp. 815-824.

*Primary Examiner* — Katherine L Fernandez
(74) *Attorney, Agent, or Firm* — UB Greensfelder LLP; Brian E. Turung

(57) ABSTRACT

Method and apparatus for determining the volemic status and vascular tone of the haemodynamic system. The method comprises: receiving a photoplethysmography (PPG) signal by a computer, which signal comprises an alternating AC component as PPG amplitude and the DC component as PPG baseline from a sensor in data communication with a living tissue; determining, in each case by a computer, a multiplicity of PPG signals from the living tissue; determining a multiplicity of AC components of the PPG signals, determining a multiplicity of DC components of the PPG signals, determining a multiplicity of AC waveforms from the AC components and identifying differences in the AC waveforms over time by comparing at least two AC waveforms; determining a DC signal trend over time by comparing at least two DC components; and determining the
(Continued)

volemic status and/or vascular tone of the haemodynamic system of the living tissue as a reaction to at least one AC waveform difference and/or a DC signal trend over time.

20 Claims, 8 Drawing Sheets

(51) Int. Cl.
  *A61B 5/02*     (2006.01)
  *A61B 5/0295*    (2006.01)
(52) U.S. Cl.
  CPC .......... *A61B 5/4836* (2013.01); *A61B 5/7264* (2013.01); *A61B 5/7275* (2013.01); *A61B 5/7278* (2013.01); *A61B 2560/0223* (2013.01)

(56) References Cited

U.S. PATENT DOCUMENTS

| 2008/0033305 | A1* | 2/2008 | Hatib | A61B 5/0285 |
| | | | | 600/485 |
| 2011/0077474 | A1* | 3/2011 | Huiku | A61B 5/02416 |
| | | | | 600/301 |
| 2012/0310100 | A1* | 12/2012 | Galen | A61B 5/7282 |
| | | | | 600/500 |
| 2013/0172759 | A1* | 7/2013 | Melker | A61B 5/682 |
| | | | | 600/476 |
| 2015/0080746 | A1* | 3/2015 | Bleich | G16H 20/30 |
| | | | | 600/479 |
| 2016/0157776 | A1* | 6/2016 | Mestha | A61B 5/02438 |
| | | | | 600/479 |
| 2019/0282179 | A1 | 9/2019 | Newberry | |
| 2022/0054031 | A1* | 2/2022 | Wong | A61B 5/6817 |

* cited by examiner

METHOD AND DEVICE FOR DETERMINING VOLEMIC STATUS AND VASCULAR TONE

BACKGROUND OF THE INVENTION

Field of the Invention

The present invention relates to a method and device for determining volemic status and vascular tone.

Discussion of Background Information

In clinical practice, the volemic status and the vascular tone of the hemodynamic system of a patient cannot be determined, or can only be determined invasively.

The photoplethysmographic (PPG) signal from pulse oximetry offers noninvasive information about the oxygen saturation and the pulse wave. The PPG waveform represents the change in the blood volume in the monitored tissue (usually the finger) during a heartbeat. This pulse flow wave is influenced and modulated significantly by vessel interactions. By way of example, forward and backward pulse pressure waves are identifiable in the PPG signal.

Changes in the contour of the PPG waveform therefore allow conclusions to be drawn about the volemic status and the vascular tone of the hemodynamic system.

However, conventional pulse oximeters are not suitable for the high resolution and accuracy demanded by the invention. By way of example, pulse oximeters lack an output of the unfiltered raw signal and an output of measured values onto a heartbeat-to-heartbeat base (beat-to-beat base), and a high time resolution.

An option for continuous and noninvasive determination of the volemic status and of the vascular tone of the hemodynamic system would be desirable.

SUMMARY OF THE INVENTION

The invention relates to a method for determining the volemic status and/or the vascular tone of the hemodynamic system, the method comprising:

sensory detection of a photoplethysmography (PPG) signal from a living tissue, the PPG signal having an alternating AC component as a PPG amplitude and a DC component as a PPG baseline, determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms;

determining a DC signal trend over time by comparing at least two DC components; and determining the volemic status and/or the vascular tone of the hemodynamic system of the living tissue as a reaction to at least one AC waveform difference and/or one direct current signal trend over time.

As an alternative or in addition, the method can be designed in such a way that the photoplethysmography (PPG) signal is recorded by one or more of the following photoplethysmographs, a pulse oximeter, a transmission-optical sensor, a reflective photo-optical sensor, a pressure transducer, a tonometry apparatus, a strain gauge, an ultrasonic apparatus, an electrical impedance measuring apparatus, blood pressure measuring equipment, an ECG apparatus and a camera/detector system.

As an alternative or in addition, the method can be designed in such a way that the computer analyzes the photoplethysmography (PPG) signal using the first or second derivative (d2DVP/dt2) of the PPG.

As an alternative or in addition, the method can be designed in such a way that the computer analyzes the signal from the photoplethysmography (PPG) using artificial neural networks, the extraction of periodic components using frequency analyses or nonlinear dynamic analyses.

As an alternative or in addition, the method can be designed in such a way that the determination of a pulse frequency from the AC component comprises:

identifying a multiplicity of signal peaks within the AC component by means of the computer;

identifying a time event for each of the multiplicity of signal peaks by means of the computer; and determining a multiplicity of time differences by means of the computer, each time difference being determined from a first time event of the first peak value and a second time event of a second peak value.

As an alternative or in addition, the method can be designed in such a way that the determination a pulse strength metric from the AC component comprises:

identifying a multiplicity of signal peaks within the AC component by means of the computer; and identifying an amplitude for each of the multiplicity of signal peaks by means of the computer.

As an alternative or in addition, the method can be designed in such a way that there is the determination of an average amplitude for at least some of the multiplicity of amplitudes by way of the computer.

As an alternative or in addition, the method can be designed in such a way that the computer analyzes the waveform of at least one AC component in order to identify at least one or more of a wave amplitude as the wave spacing from bottom to top, expressed in a scale from 0-100%, a systolic forward wave S, a diastolic backward wave D, a dichrotic notch which is determined by the analysis of the first derivative of PPG and which separates the systolic forward wave S from the diastolic backward wave D.

As an alternative or in addition, the method can be designed in such a way that the computer predicts the vascular tone of the hemodynamic system from the waveform of at least one AC component, a normal vascular tone being characterized by a waveform with a certain amplitude, with the dichrotic notch being located at between −50% of the wave amplitude.

As an alternative or in addition, the method can be designed in such a way that the computer predicts the vascular tone of the hemodynamic system from the waveform of at least one AC component, with a vasoconstriction being characterized by a low waveform amplitude in relation to the normal PPG amplitude, the dichrotic notch being located at above 50% of the wave amplitude.

As an alternative or in addition, the method can be designed in such a way that the computer predicts the vascular tone of the hemodynamic system from the waveform of at least one AC component, with a vasoconstriction being characterized by a low waveform amplitude without dichrotic notch or even being merged into the systolic pulse wave(s).

As an alternative or in addition, the method can be designed in such a way that the computer predicts the vascular tone of the hemodynamic system from the waveform of at least one AC component, with a normal vasodilation being characterized by a high waveform amplitude with the dichrotic notch being below 50% of the wave amplitude or even below zero (negative dichrotic notch).

The method as claimed in at least the preceding claims, wherein the computer predicts the volemia of the hemodynamic system from a shift of the DC component over time.

As an alternative or in addition, the method can be designed in such a way that the computer predicts the volemia of the hemodynamic system from a shift of the DC component over time, with hypervolemia being predicted if there is a shift of the DC component beyond a defined baseline over time.

As an alternative or in addition, the method can be designed in such a way that the computer predicts the volemia of the hemodynamic system from a shift of the DC component over time, with hypovolemia being predicted if there is a shift in the DC component below a defined baseline over time.

As an alternative or in addition, the method can be designed in such a way that the computer is further configured to analyze AC components of the PPG signal waveform as a measure for the vascular tone while a shift of the DC component over time is determined as a measure for volemia.

As an alternative or in addition, the method can be designed in such a way that the computer uses a second PPG sensor in data communication with a living tissue, with the second PPG sensor being arranged at a different point in the living tissue in comparison with the first sensor in order to validate data from the first sensor.

The method as claimed in at least the preceding claims, wherein the computer uses at least one other sensor 20 and such sensor data, for example an acceleration sensor 21, a tonometer, microscope, pressure or temperature sensor, in order to validate data from the first sensor.

The method as claimed in at least the preceding claims, wherein the computer uses at least one other sensor and such sensor data, for example an electrocardiogram, a noninvasive arterial blood pressure, a noninvasive arterial pulse flow/pressure waveform, capnography, oxygraphy, in order to provide complementary information for the prediction of the state of the hemodynamic system.

The method as claimed in at least one of the preceding claims, wherein the computer is further configured to receive hemodynamic standard parameters from other sensors for the purposes of a global assessment of the hemodynamics.

As an alternative or in addition, the method can be designed in such a way that the computer is further configured to verify the predicted volemia by virtue of including hemodynamic parameters, for example the noninvasive arterial blood pressure signal from other sensors 20, 30.

As an alternative or in addition, the method can be designed in such a way that the computer is further configured to verify the predicted vascular tone by virtue of including hemodynamic parameters from other sensors.

As an alternative or in addition, the method can be designed in such a way that the computer is further configured to emit light and to detect a pulse wave by way of light absorption/reflection;

perform an analog-to-digital conversion of the analog signals into digital signals;

perform pre-processing, which reduces the noise of each of the outputs of the analog-to-digital conversion step;

increase the independence between the signals;

analyze the AC and DC components of each pulse wave;

determine the specific hemodynamic state on the basis of the results of the analysis.

As an alternative or in addition, the method can be designed in such a way that the computer is further configured to carry out a PPG contour analysis which identifies wave amplitude and dichrotic notch position;

capturing changes in the DC component vis-à-vis the baseline;

determining a specific hemodynamic condition on the basis of the results of the analysis;

and calculating the amplitude a notch position and the shift of the DC component from the baseline for each pulse waveform.

As an alternative or in addition, the method can be designed in such a way that the computer is further configured to determine whether there is a relationship between the AC and the DC component of the PPG signal.

As an alternative or in addition, the method can be designed in such a way that the computer is further configured to determine a blood oxygen saturation from the PPG signal.

As an alternative or in addition, the method can be designed in such a way that the computer is further configured to calibrate the PPG signal by determining a multiplicity of PPG signals over time while the living tissue is arranged at heart level for a first time period, followed by a second time period, in which the living tissue is arranged above the heart level, and followed by a third time period, in which the living tissue is arranged below the heart level.

As an alternative or in addition, the method can be designed in such a way that the computer is further configured to calibrate the PPG signal by determining a multiplicity of PPG signals over time while the living tissue is arranged at heart level for a first time period following a second time period and/or a third time period.

As an alternative or in addition, the method can be designed in such a way that the computer is further configured to calibrate the PPG signal by determining a multiplicity of PPG signals over time, determining a multiplicity of AC components of the PPG signals and determining a multiplicity of DC components of the PPG signals while the living tissue is arranged level with a heart for a first time interval, followed by a second time interval in which the living tissue is arranged above the heart level and followed by a third time interval in which the living tissue is arranged below the heart level, wherein the computer stores values of PPG signals, including AC and DC components, from the first time interval, from the second time interval and the third time interval in order to determine the clinical range of normal values and the highest-possible and lowest-possible limit values of the PPG signals, including AC and DC components, in relation to vascular tone and volemia for a certain patient.

As an alternative or in addition, the method can be designed in such a way that the computer stores values of PPG signals from the first time period as base values and values from the second time period as lower limit for vasodilation and/or hypovolemia and values from the third time period as upper limit for vasoconstriction and/or hypervolemia for a certain patient.

The method as claimed in at least the preceding claims, wherein the time periods have the same length.

As an alternative or in addition, the method can be designed in such a way that each time period takes as long as required to obtain a stable PPG signal.

As an alternative or in addition, the method can be designed in such a way that the computer is further configured to predict, starting with, the volemic status and/or the vascular tone of the hemodynamic system for a certain patient after the calibration has been completed.

As an alternative or in addition, the method can be designed in such a way that the computer is further configured to apply a rule for alerting or not warning medical staff on the basis of the actual prediction of the volemic status and/or the vascular tone of the hemodynamic system, the medical staff being alerted if the volemic status and/or the vascular tone increases or decreases by a predetermined relative or absolute value.

The method as claimed in at least the preceding claims, wherein the method is carried out during at least one obligatory respiratory cycle, with the computer being part of a medical ventilator or being connected to a medical ventilator in order to assess the cardiopulmonary interaction induced by this equipment.

The invention also relates to an apparatus.

Apparatus for determining the volemic status and/or the vascular tone of the hemodynamic system, the apparatus comprising:

a sensor for detecting a photoplethysmography (PPG) signal from a living tissue, the PPG signal having an alternating AC component as PPC amplitude and a DC component as a PPG baseline, and a computer which is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

The apparatus for determining the volemic status and/or the vascular tone of the hemodynamic system also comprises at least one sensor with at least one light emitter and at least one light detector, with the sensor (light emitter) illuminating living tissue 0 with light at certain wavelengths and receiving light modulated by the tissue 0 by way of the detector, a computer being comprised which determines a photoplethysmography (PPG) signal or light absorption from the signal of the detector, with the computer being configured and designed to carry out the following method steps:

determining a multiplicity of PPG signals or the light absorption from the living tissue over time;

determining a multiplicity of AC components of the PPG signals or the light absorption, determining a multiplicity of DC components of the PPG signals or the light absorption, determining the volemic status and/or the vascular tone of the hemodynamic system of the living tissue 0 by analyzing the AC components and/or DC components.

Wherein the computer analyzes the photoplethysmography (PPG) signal using the first or second derivative (dDVP/dt) of the PPG.

Wherein the computer is further configured to emit light
for the purposes of detecting a pulse wave by light absorption/reflection;
for the purposes of an analog-to-digital conversion of the analog signals into digital signals;
for pre-processing purposes, which reduces the noise of each output of the analog-to-digital conversion step,
for the purposes of increasing the independence between the signals;
for the purposes of analyzing the AC and DC component of each pulse wave;
for the purposes of determining the specific hemodynamic state on the basis of the results of the analysis.

Wherein the computer is configured and designed to determine a ratio of the AC component to the DC component; V=AC/DC, where this ratio V represents the local perfusion of the tissue.

Wherein the computer is configured and designed to analyze the curve of the PPG wave in relation to maxima, in particular to identify two maxima which are separated by an indentation, the indentation representing the dichrotic notch.

Wherein the computer is configured and designed to determine the time delay ($\Delta T$) between the maxima S and D and determine a measure for the stiffness of the arteries from the time delay ($\Delta T$) between the maxima S and D.

Wherein the computer is configured and designed to determine an amplitude of the first maximum S and an amplitude of the second maximum D, with the computer determining the ratio of the amplitude of the first maximum S to the amplitude of the second maximum D as systemic vascular resistance.

Wherein the computer is configured and designed to determine a maximum percentage PPG amplitude which equals 00% and sub-maximal percentage PPG amplitudes of the order of below or above 0%.

Wherein the computer is configured and designed to determine a vasoconstriction if no dichrotic notch can be identified in the curve of the PPG signal and/or determine vasodilation if a dichrotic notch can be identified in the curve of the PPG signal.

Wherein the computer is configured and designed to
determine a multiplicity of PPG signals from the living tissue by means of the computer;
determine a multiplicity of DC components of the PPG signals by means of the computer,
determine a DC signal trend over time by means of the computer by comparing at least two DC components; and
determine a DC signal trend over time which corresponds to a normal volemic status and form a normal range for DC values,
identify DC signals which depart from the normal range for DC values,
determine a hypervolemia for DC signals which depart upwardly from the normal range for DC values (in the direction of one),
determine a hypovolemia for DC signals which depart downwardly from the normal range for DC values (in the direction of zero).

Wherein the computer is configured and designed to
determine a multiplicity of PPG signals from the living tissue by means of the computer;
determine a multiplicity of AC components of the PPG signals by means of the computer, determine an AC signal trend over time by means of the
computer by comparing at least two AC components;
and determine an AC signal trend over time which corre-
sponds to a normal vascular tone and form a normal
range for AC values, identify AC signals which depart from the normal range
for AC values, determine a vasoconstriction for AC signals which depart
downwardly from the normal range for AC values (in
the direction of zero), determine a vasodilation for AC signals which depart
upwardly from the normal range for AC values (in the
direction of one).

Wherein the computer is configured and designed to
identify a normal PPG shape if the dichrotic notch is
between 0% and % of the entire, maximum PPG amplitude.

Wherein the apparatus comprises:

a computer for receiving a photoplethysmography (PPG)
signal which comprises an alternating AC component
as PPG amplitude and the DC component as PPG
baseline from a sensor in data communication with a
living tissue 0;

determining a multiplicity of PPG signals over time from
the living tissue by means of the computer;

determining a multiplicity of AC components of the PPG
signals by means of the computer, determining a multiplicity of DC components of the PPG
signals by means of the computer, determining a multiplicity of AC waveforms from the AC
components by means of the computer, and identifying
differences in the AC waveforms over time by com-
paring at least two AC waveforms;

determining a DC signal trend over time by means of the
computer by comparing at least two DC components;
and determining the volemic status and/or the vascular tone of
the hemodynamic system of the living tissue 0 by the
computer as a reaction to at least one AC waveform
difference and/or one DC signal trend over time.

The invention also relates to an apparatus for determining
the volemic status and/or the vascular tone of the hemody-
namic system, wherein the apparatus comprises:

a computer for receiving a photoplethysmography (PPG)
signal which comprises an alternating AC component
as PPG amplitude and the DC component as PPG
baseline from a sensor in a data communication with a
living tissue;

determining a multiplicity of PPG signals over time from
the living tissue by means of the computer;

determining a multiplicity of AC components of the PPG
signals by means of the computer, determining a multiplicity of DC components of the PPG
signals by means of the computer, determining a multiplicity of AC waveforms from the AC
components by means of the computer, and identifying
differences in the AC waveforms over time by com-
paring at least two AC waveforms;

determining a DC signal trend over time by means of the
computer by comparing at least two DC components;
and determining the volemic status and/or the vascular tone of
the hemodynamic system of the living tissue by means
of the computer as a reaction to at least one AC
waveform difference and/or one DC signal trend over
time.

The invention also relates to a system. The system com-
prises at least one ventilator, an apparatus for determining
the volemic status and/or the vascular tone of the hemody-
namic system, and a computer.

The apparatus for determining the volemic status and/or
the vascular tone of the hemodynamic system and a venti-
lator may also be a part of a system according to the
invention or constitute the said system.

The invention also relates to a computer program com-
prising instructions which, when the program is executed by
a computer, prompt the computer to carry out the method.

The invention also relates to a computer-readable medium
comprising instructions which, when executed by a com-
puter, cause the computer to carry out the method. The
technology according to the invention is related to photop-
lethysmography (PPG), as is conventional in commercial
pulse oximeters, for example in typical transmission pulse
oximeters for fingers. The PPG wave corresponds to the
absorption of light by tissue in the finger according to the
Beer-Lambert law. The absorbed signal is based on two
components: a pulsatile component (AC), which represents
the pulse pressure wave, and a non-pulsatile component
(DC), which represents venous blood, nails, bones, skin and
soft tissue.

The principal differences between the PPG technology
required according to the invention and standard pulse
oximeters are the following:

1. Lack of filters that are applied to the raw signal
2. Lack of automatic zeroing of the baseline (the signal
   can usually vary during the recording thereof)
3. Output of the measured values on a heartbeat-to-
   heartbeat base (beat-to-beat base)
4. SpO2 values with one decimal place
5. Good waveform definition
6. High time resolution
7. AC and DC data are at least available on a beat-to-beat
   basis These hardware features in combination allow many
different analyses of the PPG raw curves using specific
software solutions that are carried out by the computer. PPG
represents the noninvasive FLOW pulse wave (which is
similar to the PRESSURE pulse wave that is obtained by an
intra-arterial catheter). The shape of the PPG—i.e., defined
by amplitude, width and position of the dichrotic notch in
the AC component—is related to the changes in the arterial
blood pressure which are caused by the change in the
vascular tone.

The PPG can identify arterial hypertonia and hypotonia,
which are caused by vasoconstriction/vasodilation, with a
high sensitivity and specificity (97.8% and 98.4%, respec-
tively). The novelty of this approach lies in its unique
capability of monitoring the vascular tone; a noninvasive
diagnostic capability which hitherto was only available to
patients, who receive advanced hemodynamic monitoring
for the purposes of calculating the systemic vascular resis-
tance, using invasive means. Our PPG waveform analysis
offers an unprecedented noninvasive option for deriving
beat-to-beat information about the vascular tone at the
patient's bed.

The DC component is influenced by two components:

1. FIXED light absorption by the tissue and
2. DYNAMIC light absorption by the venous blood.

Consequently, each change in the DC component is
caused by a change in the volume of the venous blood in the
finger (the dynamic path). According to our measurements
on patients, these changes are linked to changes in the
volume state. Therefore, the DC component should be used both in the operating theater and in the intensive care unit for the purposes of diagnosing and monitoring the volemia or preload dependence of a patient.

Combined monitoring of both the AC and the DC component supplies clinically relevant information about changes in the vascular tone and volemic state. By way of the integration in one diagnostic and monitoring instrument, it is possible to identify various causes such as vasoconstriction, normal vascular tone, vasodilation, hypovolemia, normovolemia and hypervolemia, and hence the physiopathological mechanisms of arterial blood hypertonia and hypotonia. This type of monitoring is very innovative since it is implemented completely noninvasively and in real time.

The proposed analysis of the AC/DC components can be represented in automated fashion and online, as a result of which physicians receive diagnostic information, or even potential treatments. This monitoring solution will enable "individualized, personalized medicine".

The technology described, specifically the application of PPG technology for the purposes of identifying information about the vascular tone and volemic state for use in medical ventilation contains:

A combined analysis of both the AC and the DC component in a single monitoring instrument in order to recognize the various hemodynamic states and propose possible solutions (such as the infusion of fluids or the use of vasoconstrictors, etc.)

A specific calibration maneuver which is based on raising and lowering the extremity wearing the PPG sensor and which triggers vessel reflexes The technology is based on the concept of being able to use the DC signal in order to recognize the preload dependence or the fluid reaction in the case of critically ill patients in the context of a DYNAMIC maneuver such as increasing the PEEP, maneuver for lifting the legs, etc.

The high correlation between the PPG amplitude and the arterial blood pressure possibly predicting/improving/assisting noninvasive systems for noninvasive measurement of the arterial blood pressure The PPG possibly also being obtained in the mid to low esophagus with the aid of reflective oximetry. The proposed AC analysis could noninvasively identify changes in the mesenteric perfusion.

It is to be noted that the features listed individually in the claims may be combined with one another in any technically advantageous manner and thus highlight further embodiments of the invention. The description additionally characterizes and specifies the invention, especially in conjunction with the figures.

It further is to be noted that an "and/or" conjunction found between two features and linking these, as used herein, should always be interpreted in such a way that only the first feature may be present in a first embodiment of the subject matter according to the invention, only the second feature may be present in a second embodiment, and both the first and the second feature may be present in a third embodiment.

Provided there is no other express description, a computer can be understood to mean any computing equipment intended for interaction with one of the measuring devices for measured data from a living being. In particular, a computer can be understood to be a chip or control unit of a ventilator or of a pulse oximeter that is at least indirectly connectable to a ventilator. In some cases, the computer may collaboratively consist of a chip or the control unit of a ventilator or of at least one chip or the control unit of a pulse oximeter that is at least indirectly connectable to a ventilator.

In particular, a computer can be in the form of a chip or control unit of an apparatus for determining the volemic status and/or in the form of a chip or control unit of an apparatus for determining the vascular tone of the hemodynamic system.

Within the meaning of the invention, waveforms are signal curves recorded by the apparatus for determining the volemic status and/or the vascular tone of the hemodynamic system, in particular a photoplethysmography (PPG) signal or a light absorption or an AC signal or a DC signal.

A ventilator is to be understood to mean any piece of equipment which assists a user or patient with natural respiration, undertakes the ventilation of the user or living being (e.g., patient and/or newborn and/or premature baby) and/or is used for respiratory therapy and/or influences the respiration of the user or patient in another way. By way of example, but without being an exhaustive list, these include CPAP and BiPAP machines, anesthetic machines, respiratory therapy equipment, (clinical, outpatient or emergency) ventilators, high-flow therapy equipment and cough machines. Ventilators can also be understood to mean diagnostic equipment for ventilation. Said diagnostic equipment can generally be used to measure medical and/or respiration-based parameters of a living being. These also include equipment which can measure and optionally process medical parameters of patients in combination with respiration or only in relation to respiration.

BRIEF DESCRIPTION OF THE DRAWINGS

The invention is described in more detail in exemplary fashion on the basis of FIGS. 1 to 8.

DETAILED DESCRIPTION OF EMBODIMENTS OF THE INVENTION

Figure 1:
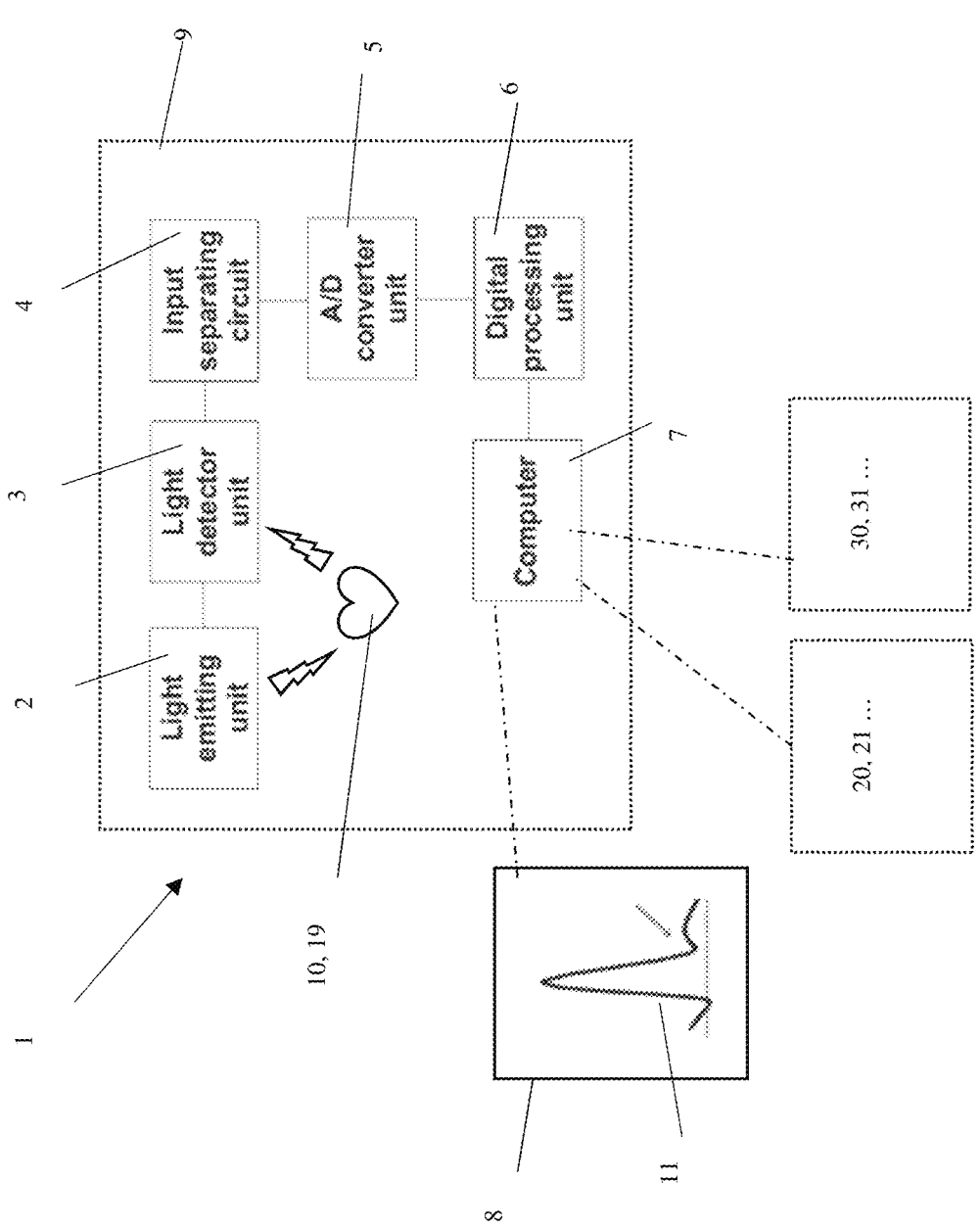
FIG. 1 schematically shows the method according to the invention and the apparatus for determining the volemic status and/or the vascular tone of the hemodynamic system.

FIG. 1 shows the method according to the invention for determining the volemic status and/or the vascular tone of the hemodynamic system and the apparatus for determining the volemic status and/or the vascular tone of the hemodynamic system.

A photoplethysmography (PPG) signal 11 is generated and recorded by one or more of the following apparatuses 1: a photoplethysmograph, a pulse oximeter, a transmission-optical sensor, a reflective photo-optical sensor, a pressure transducer, a tonometry apparatus, a strain gauge, an ultrasonic apparatus, an electrical impedance measuring apparatus, blood pressure measuring equipment, an ECG apparatus and a camera/detector system. The aforementioned apparatuses may be part of a medical ventilator or may be connected to a medical ventilator. The apparatus for determining the volemic status and/or the vascular tone of the hemodynamic system and a ventilator may also be part of a system according to the invention or make up the said system.

The apparatus 1 for determining the volemic status and/or the vascular tone of the hemodynamic system comprises a sensor 9 having a light emitter 2 and a light detector 3. The sensor illuminates (light emitter 2) living tissue 10 with light at certain wavelengths and receives light modulated by the tissue 10 by way of the detector 3. A computer 7 determines a photoplethysmography (PPG) signal 11 from the signal of the detector 3. A light source 2 emits light at living tissue 10 (for example, a finger, a forehead or the like) and a detector 3 receives at least some of the light modulated by the tissue. The modulated light may be or comprise transmitted and/or reflected and/or refractive light. Various electronic components 4, 5, 6 that prepare the signal for the computer 7 may be connected downstream of the detector.

The computer is configured and designed to carry out the following steps:

determining a multiplicity of PPG signals from the living tissue over time by means of the computer 7;

determining a multiplicity of AC components of the PPG signals by means of the computer 7, determining a multiplicity of DC components of the PPG signals by means of the computer 7, determining a multiplicity of AC waveforms from the AC components by means of the computer 7, and identifying differences in the AC waveforms over time by way of comparing at least two AC waveforms;

determining a DC signal trend over time by the computer 7 by way of comparing at least two DC components; and determining the volemic status and/or the vascular tone of the hemodynamic system of the living tissue 10 by means of the computer 7 as a reaction to at least one AC waveform difference and/or one DC signal trend over time.

The computer analyzes the photoplethysmography (PPG) signal using the first or second derivative (d2DVP/dt2) of the PPG.

The computer analyzes the signal from the photoplethysmography (PPG) using artificial neural networks, the extraction of periodic components using frequency analyses or nonlinear dynamic analyses.

The determination of a pulse frequency from the AC component comprises:

identifying a multiplicity of signal peaks within the AC component by means of the computer 7;

identifying a time event for each of the multiplicity of signal peaks by means of the computer 7; and determining a multiplicity of time differences by means of the computer 7, each time difference being determined from a first time event of the first peak value and a second time event of a second peak value.

The determination a pulse strength metric from the AC component comprises:

identifying a multiplicity of signal peaks within the AC component by means of the computer 7; and identifying an amplitude for each of the multiplicity of signal peaks by means of the computer 7.

The computer 7 is further configured to receive hemodynamic standard parameters from other sensors 20, 30 for global assessment of the hemodynamics.

The computer 7 is further configured to verify the predicted volemia by virtue of including hemodynamic parameters, for example the noninvasive arterial blood pressure signal from other sensors 20, 30.

The computer 7 is further configured to verify the predicted vascular tone by virtue of including hemodynamic parameters from other sensors 20, 30.

The computer 7 is further configured to emit light for the purposes of detecting a pulse wave by light absorption/reflection;

for the purposes of an analog-to-digital conversion of the analog signals into digital signals;

for pre-processing purposes, which reduces the noise of each output of the analog-to-digital conversion step, for the purposes of increasing the independence between the signals;

for the purposes of analyzing the AC and DC component of each pulse wave;

for the purposes of determining the specific hemodynamic state on the basis of the results of the analysis.

The computer 7 is further configured to determine a blood oxygen saturation from the PPG signal.

Figures 2A, 2B:
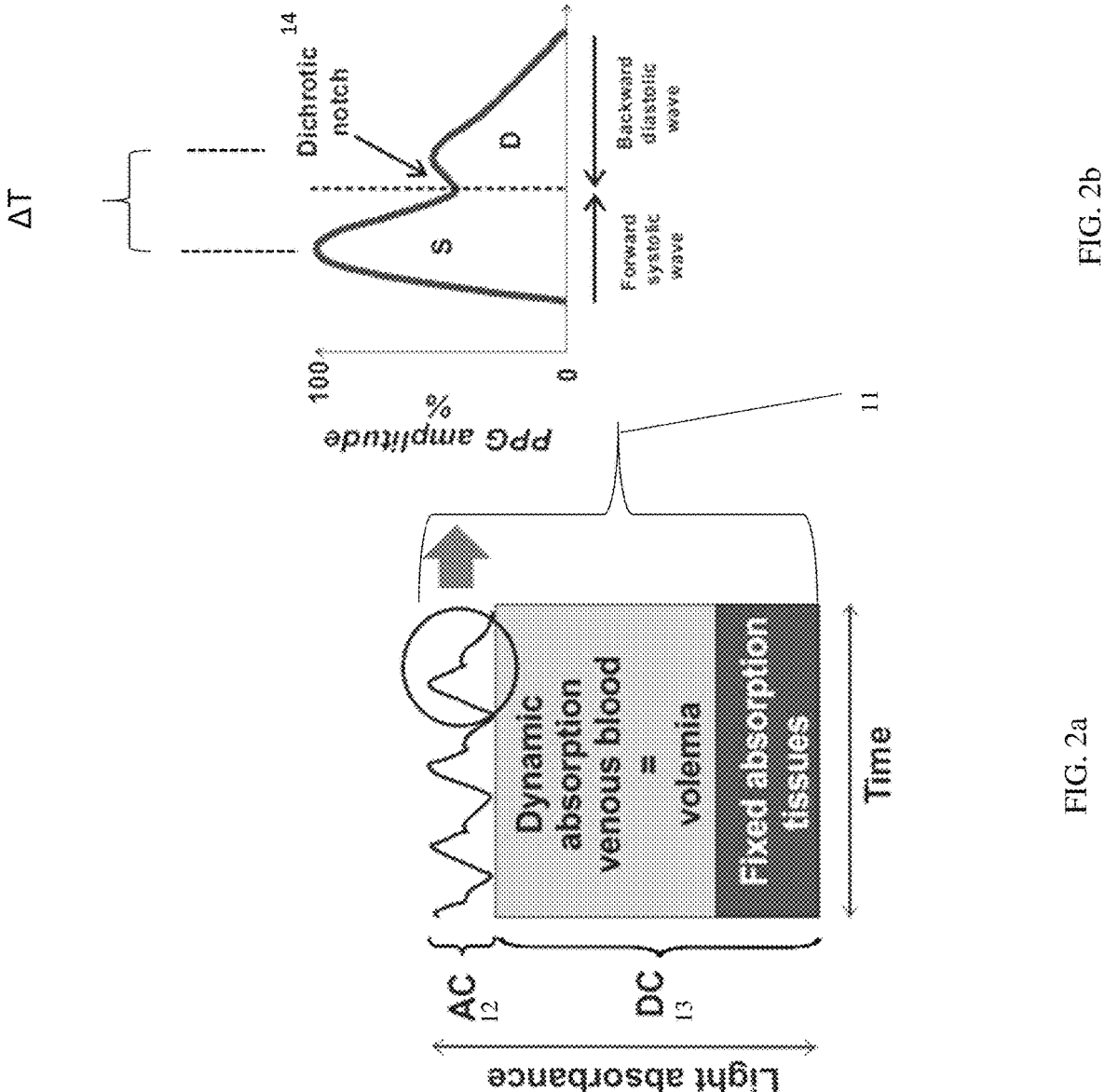
FIG. 2*a* shows the different light absorption of the various tissue constituents.
FIG. 2*b* shows a PPG amplitude in % over time for a pulsating (AC) constituent.

FIG. 2a shows the different light absorption of the various tissue constituents. The ability of pulse oximetry to detect $SpO_2$ from arterial blood only is based on the principle that the amount of absorbed red and infrared light varies with each heartbeat. During an increasing arterial blood volume during the systole, that is to say the tensioning or blood outflow phase of the heart, the blood volume and hence absorption increases, while it reduces again during the diastole.

In contrast thereto, the blood volume in the veins and capillaries, and in the skin, the fat, the bone, etc., remains relatively constant. At the same time, for the absorption of light, this means that veins, capillaries, bones and other tissue constituents absorb incident light relatively constantly—as a measured value, it may be considered to be a pure direct current (DC) signal 13 over the duration of a single heartbeat. By contrast, arterial blood absorbs the light to a different extent—due to the pulsating volume change within one heartbeat—as a result of which an alternating current (AC) signal 12 arises in addition to the DC signal likewise present. FIG. 2a shows a cross-sectional diagram of an artery and vein during the systole and diastole, and illustrates the non-pulsating (DC) 13 and pulsating (AC) 12 sections of arteries and the relative lack of changes in volume in the veins and capillaries. Consequently, a distinction should be made between the pulsating (AC) and non-pulsating (DC) blood vessels, with only the arteries having a pulsating (AC) 12 constituent. Pulse oximeters use the alternating voltage component of the light absorptions in order to determine the modulation ratio between red and IR, and calculate both oxygen saturation and heart rate therefrom. Here, as a matter of principle, only the pulsating change in the measurement data should be considered for the calculation of the heart rate.

According to the invention, the apparatus 1 for determining the volemic status and/or the vascular tone of the hemodynamic system therefore comprises a sensor 9 having a light emitter 2 and a light detector 3. The sensor illuminates (light emitter 2) living tissue 10 with light at certain wavelengths and receives light modulated by the tissue 10 by way of the detector 3. A computer 7 determines a photoplethysmography (PPG) signal 11 or a light absorption from the signal of the detector 3. Various electronic components 4, 5, 6 that prepare the signal for the computer 7 may be connected downstream of the detector.

The computer is configured and designed to carry out the following steps:

determining an AC component 12 from the PPG signal or the light absorption, determining a DC component 13 from the PPG signal or the light absorption.

The computer is also configured and designed to determine a ratio of the AC component 12 to the DC component 13; V=AC/DC. This ratio V represents the local perfusion of the tissue. Values below 1.5 indicate poor perfusion in this case.

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

FIG. 2*b* shows the PPG amplitude in % over time for the pulsating (AC) 12 constituent. The curve of the PPG wave has two maxima, which are separated by an indentation. The indentation represents the dichrotic notch 14. The first wave S is based on the systolic (forward) wave and the second wave is based on the diastolic (backward) wave.

The apparatus 1 for determining the volemic status and/or the vascular tone of the hemodynamic system therefore comprises a sensor 9 having a light emitter 2 and a light detector 3. The sensor illuminates (light emitter 2) living tissue 10 with light at certain wavelengths and receives light modulated by the tissue 10 by way of the detector 3. A computer 7 determines a photoplethysmography (PPG) signal 11 from the signal of the detector 3. A light source 2 emits light at living tissue 10 (for example, a finger, a forehead or the like) and a detector 3 receives at least some of the light modulated by the tissue. The modulated light may be or comprise transmitted and/or reflected and/or refractive light. Various electronic components 4, 5, 6 that prepare the signal for the computer 7 may be connected downstream of the detector.

The computer is configured and designed to carry out the following steps:

determining a multiplicity of AC components 12 of the PPG signals, determining a multiplicity of DC components 13 of the PPG signals.

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

Moreover, the computer is configured and designed to determine a percentage PPG amplitude from the AC component. The computer is also configured and designed to analyze the curve of the PPG wave in relation to maxima, in particular to identify two maxima which are separated by an indentation, the indentation representing the dichrotic notch 14. The computer is configured and designed to identify a first maximum S on the basis of the systolic (forward) wave and to identify a second maximum D on the basis of the diastolic (backward) wave.

The computer is configured and designed to determine the time delay (ΔT) between the maxima S and D.

The time delay between the maxima (ΔT) depends on the stiffness of the arteries. The ratio of the amplitudes of the B. The computer is configured and designed to determine a measure for the stiffness of the arteries from the time delay (ΔT) between the maxima S and D.

The computer is configured and designed to determine an amplitude of the first maximum S and an amplitude of the second maximum D. The ratio the amplitude of the first maximum S to the amplitude of the second maximum D is related to the systemic vessel resistance. The computer is therefore configured and designed to determine a measure for systemic vessel resistance from the ratio of the amplitude of the first maximum S to the amplitude of the second maximum D.

Figure 3A:
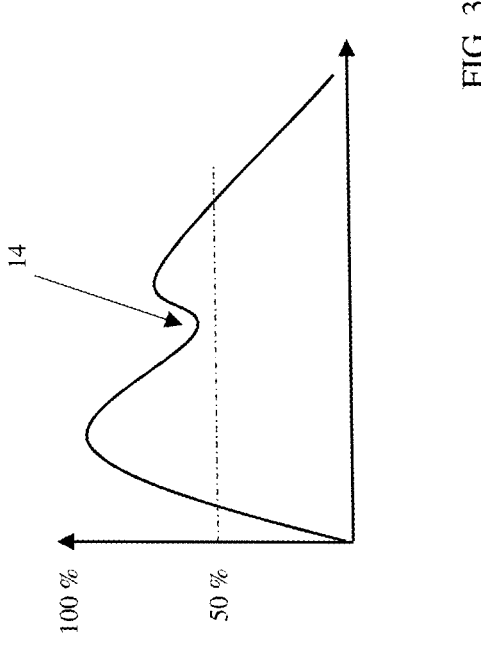
FIGS. 3*a* and 3*b* show the waveforms according to FIG. 2*b* with different dichrotic notches.
Figure 3B:
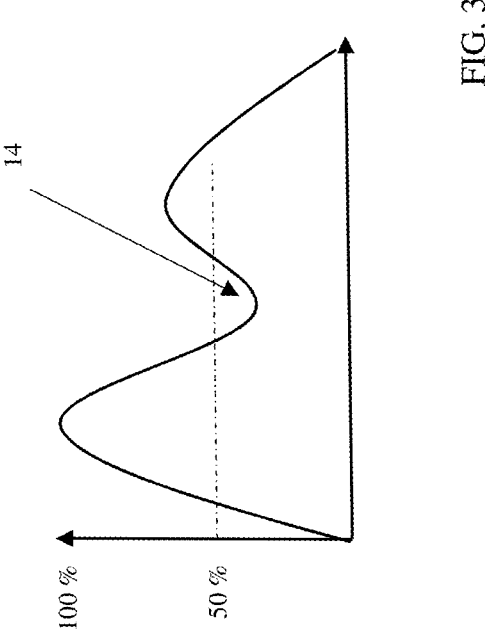

FIGS. 3*a* and 3*b* show the waveforms according to FIG. 2*b* with different dichrotic notches 14. FIGS. 3*a* and 3*b* show the PPG amplitude in % over time for the pulsating (AC) 12 constituent. The curve of the PPG wave has two maxima, which are separated by an indentation 14. The indentation represents the dichrotic notch 14. The dichrotic notch 14 is below 50% of the maximum PPG amplitude in FIG. 3*a*. In FIG. 3*b*, the dichrotic notch 14 is above 50% of the maximum PPG amplitude.

The apparatus 1 for determining the volemic status and/or the vascular tone of the hemodynamic system in this case comprises a sensor 9 having a light emitter 2 and a light detector 3. The sensor illuminates (light emitter 2) living tissue 10 with light at certain wavelengths and receives light modulated by the tissue 10 by way of the detector 3. A computer 7 determines a photoplethysmography (PPG) signal 11 from the signal of the detector 3. A light source 2 emits light at living tissue 10 (for example, a finger, a forehead or the like) and a detector 3 receives at least some of the light modulated by the tissue. The modulated light may be or comprise transmitted and/or reflected and/or refractive light.

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

The computer is moreover configured and designed to determine a percentage PPG amplitude. The computer is moreover configured and designed to determine a maximum percentage PPG amplitude, which equals 100%, and to determine sub-maximal percentage PPG amplitudes. The computer is also configured and designed to analyze the curve of the PPG wave for maxima and, in particular, to identify two maxima separated by an indentation 14, with the indentation representing the dichrotic notch 14. The computer is configured and designed to identify a first maximum S on the basis of the systolic (forward) wave and to identify a second maximum D on the basis of the diastolic (backward) wave, and to identify a dichrotic notch 14 between the maxima. Moreover, the computer is configured and designed to determine a maximum percentage PPG amplitude and sub-maximal percentage PPG amplitude of the order of below or above 50%.

Figure 4:
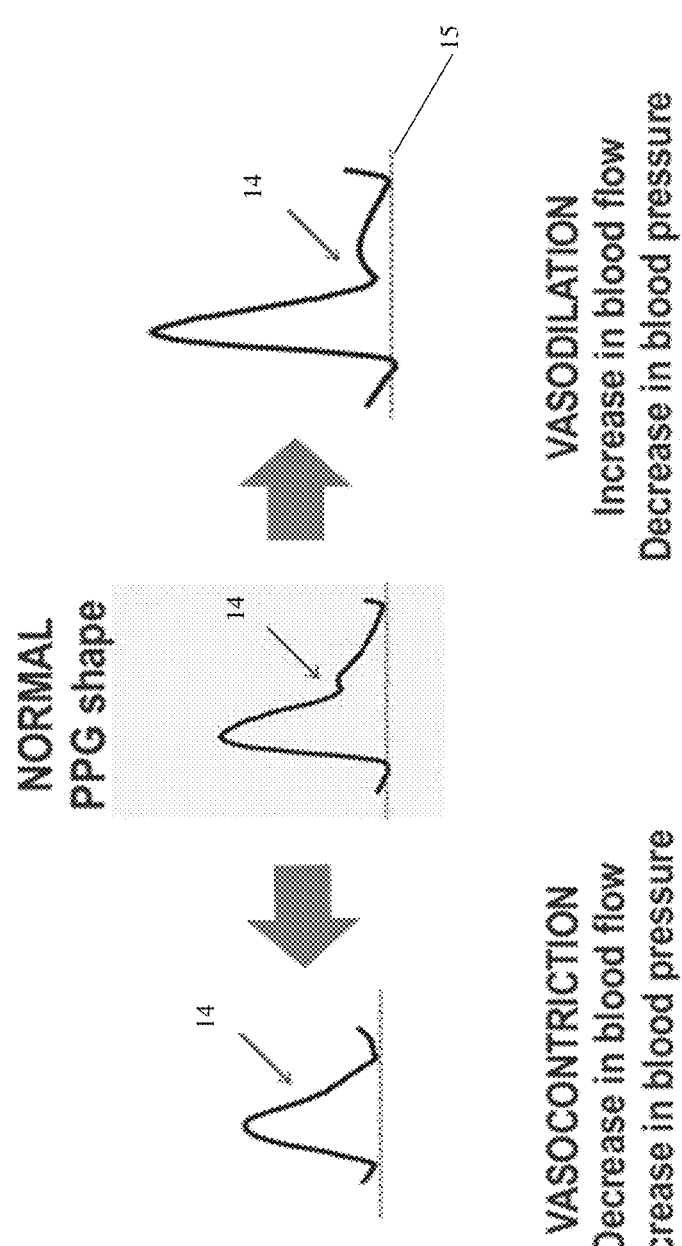
FIG. 4 shows normal PPG waveforms and PPG waveforms typical for vasoconstriction or PPG waveforms typical for vasodilation.

FIG. 4 shows normal PPG waveforms (center) and PPG waveforms typical for vasoconstriction (left) or PPG waveforms typical for vasodilation (right). It is conspicuous in this case that the dichrotic notch 14 only occurs in the case of the normal PPG waveform and in the case of the PPG waveform relating to vasodilation. The dichrotic notch cannot be found in the case of vasoconstriction.

The apparatus according to the invention for determining the volemic status and/or the vascular tone of the hemodynamic system to this end comprises a computer 7 for receiving a photoplethysmography (PPG) signal 11 which contains an alternating AC 12 component and a DC 13 component from a sensor 2, 3, 9 in data communication with a living tissue 10.

By way of example, the apparatus is configured to determine a multiplicity of PPG signals over time from the living tissue by means of the computer 7.

By way of example, the apparatus is configured to determine a multiplicity of AC components of the PPG signals by means of the computer 7 and to determine a multiplicity of DC components of the PPG signals by means of the computer 7.

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

The computer is moreover configured and designed to determine a percentage PPG amplitude or the curve of a PPG signal. The computer is also configured and designed to analyze the curve of the PPG signal for maxima and, in particular, identify two maxima which are separated by an indentation 14, with the indentation representing the dichrotic notch 14. By way of example, the computer is configured and designed to identify a first maximum S on the basis of the systolic (forward) wave and to identify a second maximum D on the basis of the diastolic (backward) wave, and to identify the dichrotic notch 14 between the maxima. The computer is moreover configured and designed to determine a vasoconstriction if no dichrotic notch 14 can be identified from the curve of the PPG signal. Moreover, the computer is configured and designed to determine a vasodilation if a dichrotic notch 14 can be identified from the curve of the PPG signal. By way of example, the apparatus is configured to verify a vasoconstriction by virtue of determining the blood pressure, with a vasoconstriction being identified if the curve of the PPG signal has no dichrotic notch 14 and, moreover, the blood pressure is rising.

By way of example, the apparatus is configured to verify a vasodilation by virtue of determining the blood pressure, with a vasodilation being identified if the curve of the PPG signal has a dichrotic notch 14 and, moreover, the blood pressure is dropping.

What emerges from an overview of FIGS. 3 and 4 is that the apparatus for example is configured to classify the vascular tone on the basis of the photoplethysmography waveform shape. The classification is based on the amplitude of the photoplethysmography (PPG) (FIG. 4) and on the position of the dichrotic notch (FIG. 3).

The apparatus is configured to identify a normal PPG shape and a vasodilation and a vasoconstriction:

The apparatus is configured to identify a normal PPG shape if the dichrotic notch 14 is between 20 and 55%, preferably 30-50%, of the entire PPG amplitude. Vasodilation increases the PPG amplitude since the tissue has a greater blood flow (a higher infrared light absorption). In the case of slight vasodilation, the notch 14 reaches the baseline 15, even though the backward wave still is obvious. The notch 14 is missing in the case of pronounced vasodilation and the notch becomes negative (drops below the baseline 15) in the case of very pronounced vasodilation.

The vasoconstriction (FIG. 4, left) shows a lower PPG amplitude than normal, meaning that the blood flow reduces (less infrared light absorption).

The notch 14 increases to above 50% of the entire PPG amplitude and melts into the systolic pulse peak.

Figure 5:
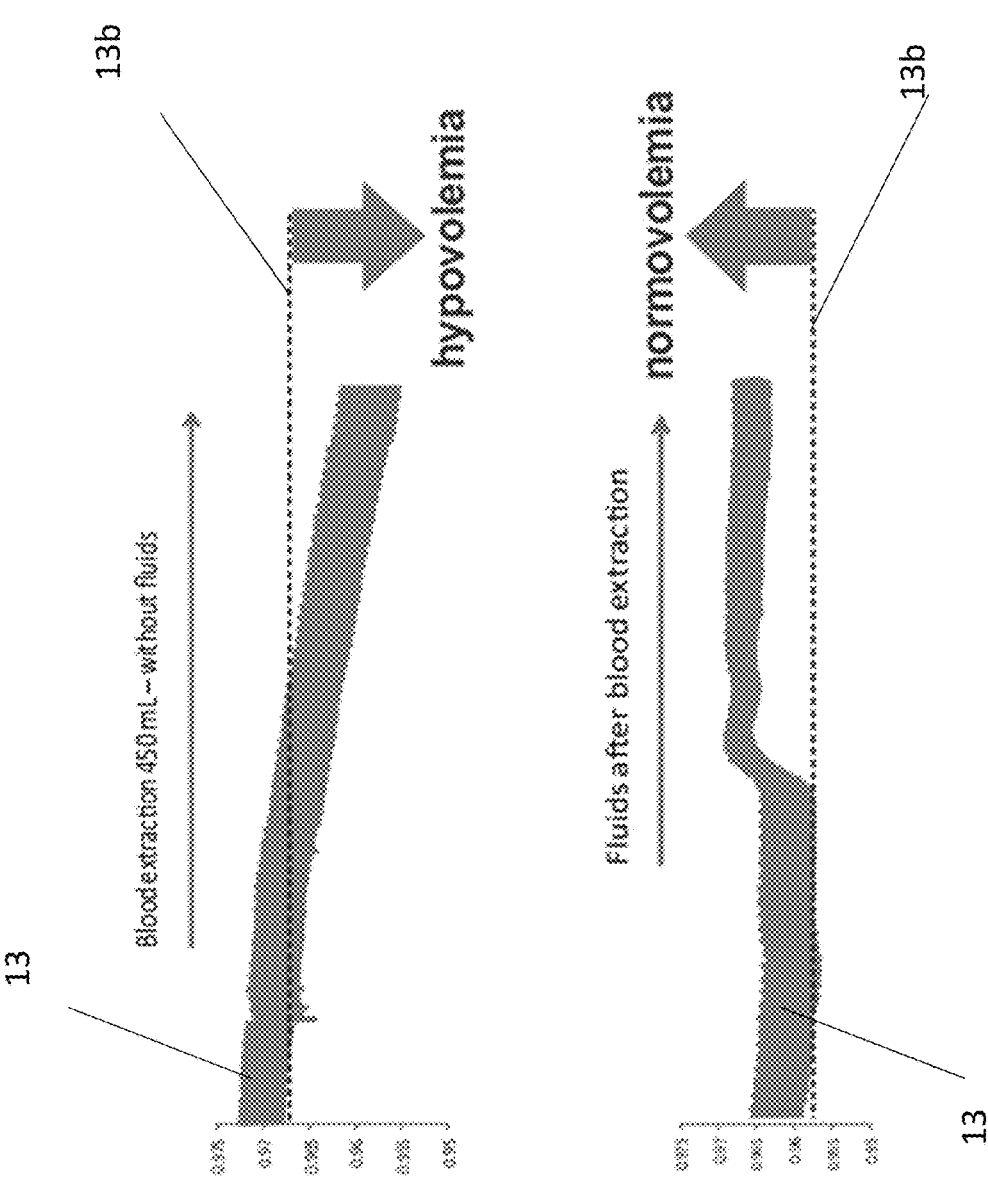
FIG. 5 shows a DC current signal over time when there is a change in the blood volume.

FIG. 5 shows the DC current signal (DC) 13 over time when there is a change in the blood volume. It is evident from the upper drawing that the DC signal reduces after 450 ml blood have been taken (hypovolemia).

It is evident from the lower drawing how the direct current signal (DC) 13 increases over time if (after blood has been taken) fluid is supplied (normovolemia). According to the invention, the identification of the volemic status is based thereon. The apparatus according to the invention for determining the volemic status and/or the vascular tone of the hemodynamic system to this end comprises a computer 7 for receiving a photoplethysmography (PPG) signal 11 which contains at least one DC component 13 from a sensor 2, 3, 9 in data communication with a living tissue 10.

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

By way of example, the apparatus is configured to determine a DC 13 signal over time from the living tissue by means of the computer 7.

Moreover, the apparatus is configured to define the curve of a DC 13 signal (over time) as baseline 13*b*, with the baseline 13*b* having substantially no change in the DC signal over time (for at least 10 seconds, preferably for at least 30 seconds).

The apparatus is moreover configured to determine a deviation from the baseline 13*b* from the curve of a DC 13 signal (over time), with a drop of the DC signal below the baseline 13*b* being assessed as hypovolemia if the drop of the DC signal below the baseline 13*b* has a duration of at least 10 seconds, preferably at least 30 seconds or more, with an increase in the DC signal above the baseline 13*b* being assessed as hypervolemia if the increase in the DC signal above the baseline 13*b* has a duration of at least 10 seconds, preferably at least 30 seconds or more, and with an increase in the DC signal to a stored baseline 13*b* being assessed as normovolemia if the increase of the DC signal to the baseline 13*b* occurs when a hypovolemia was identified previously, the latter having a duration of at least 10 seconds, preferably at least 30 seconds or more, and an increase in the DC signal was subsequently identified.

Figure 6:
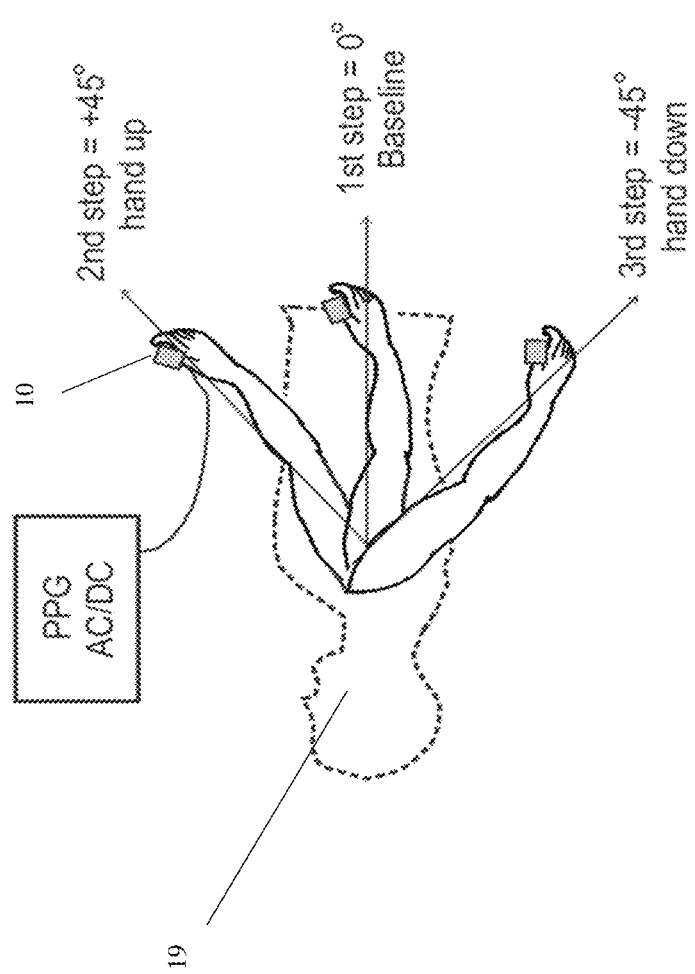
FIG. 6 and FIG. 7 illustrate the calibration of a PPG measurement for determining the volemia.
Figure 7:
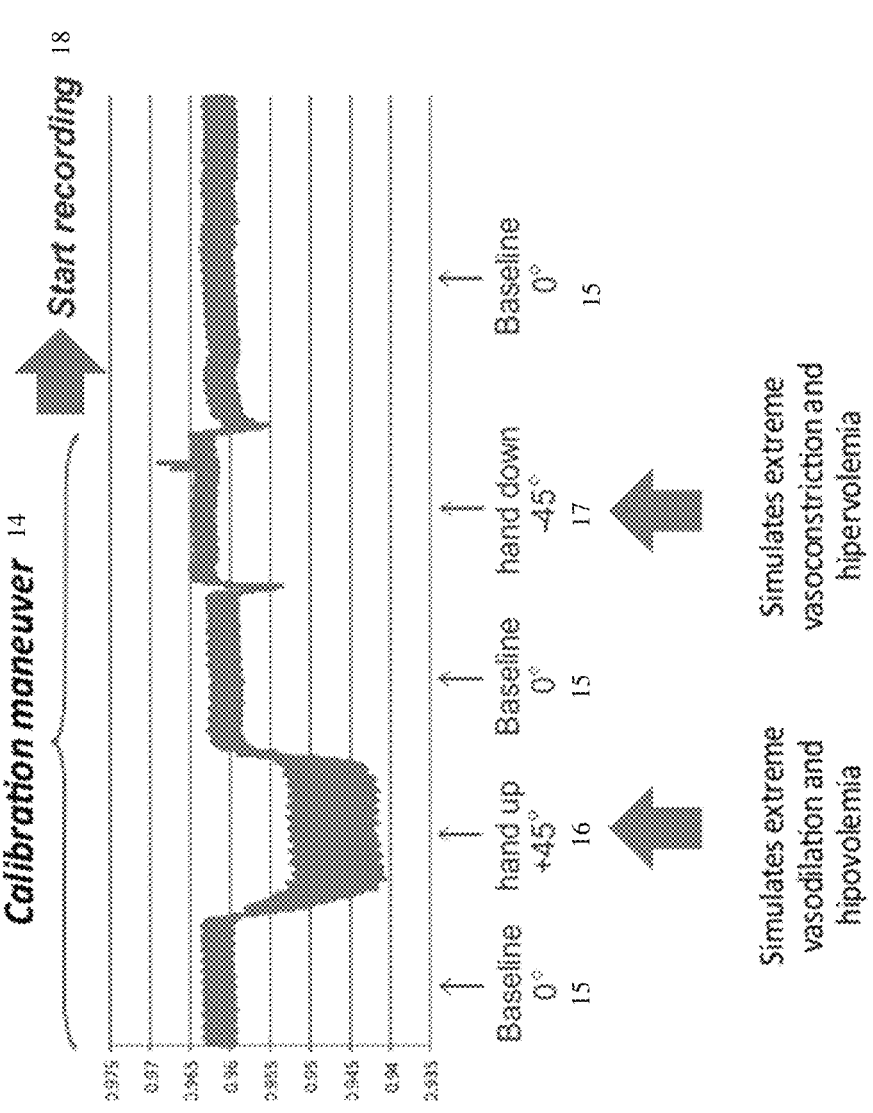

FIG. 6 and FIG. 7 illustrate the calibration 14 of the PPG measurement for determining the volemia.

To this end, the lying-down patient must initially hold the hand or the arm with the PPG sensor level with the heart so that—at an angle of 0°—there can be a determination of the PPG base signal 15. The PPG base signal 15 is stored in the apparatus.

Then, the hand is raised at an angle of 45° in order to simulate vasodilation and hypovolemia. In this position, the PPG signal is determined for vasodilation and hypovolemia 16. The PPG signal representing vasodilation and hypovolemia 16 is stored in the apparatus.

Subsequently, there is a renewed determination of the PPG base signal 15. This is followed by the hand being lowered 45° downward, as a result of which blood flows into the hand in order to simulate vasoconstriction and hypervolemia. The PPG signal for vasoconstriction and hypervolemia 17 is determined in this position. The PPG signal representing vasoconstriction and hypervolemia 17 is stored in the apparatus. Subsequently, there is a renewed determination of the PPG base signal 15. Subsequently, the apparatus monitors the volemic status and/or the vasoconstriction or vasodilation by a determination 18 of the PPG signal, in particular the DC component thereof, over time.

The apparatus according to the invention for determining the volemic status and/or the vascular tone of the hemodynamic system to this end comprises a computer 7 for receiving a photoplethysmography (PPG) signal which contains at least one DC signal component from a sensor 2, 3, 9 in data communication with a living tissue 10. By way of example, the apparatus is configured to determine a DC signal over time from the living tissue by means of the computer 7.

The computer is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

The apparatus is moreover configured to define the curve of a DC signal (over time) as base signal 15, with the base signal 15 having substantially no change in the DC signal over time (for at least 10 seconds, preferably for at least 30 seconds).

The apparatus is moreover configured to determine from the curve of a DC signal (over time) a deviation from the base signal 15, with a drop in the DC signal below the base signal 15 being assessed as hypovolemia if the drop of the DC signal below the base signal 15 has a duration of at least 10 seconds, preferably at least 30 seconds or more, with an increase in the DC signal above the base signal 15 being assessed as hypervolemia if the increase of the DC signal above the base signal 15 has a duration of at least 10 seconds, preferably at least 30 seconds or more. What emerges from the comparison of the exemplary embodiments in FIGS. 5, 6 and 7 is that the baseline 13*b* may substantially correspond to the base signal 15.

Figure 8:
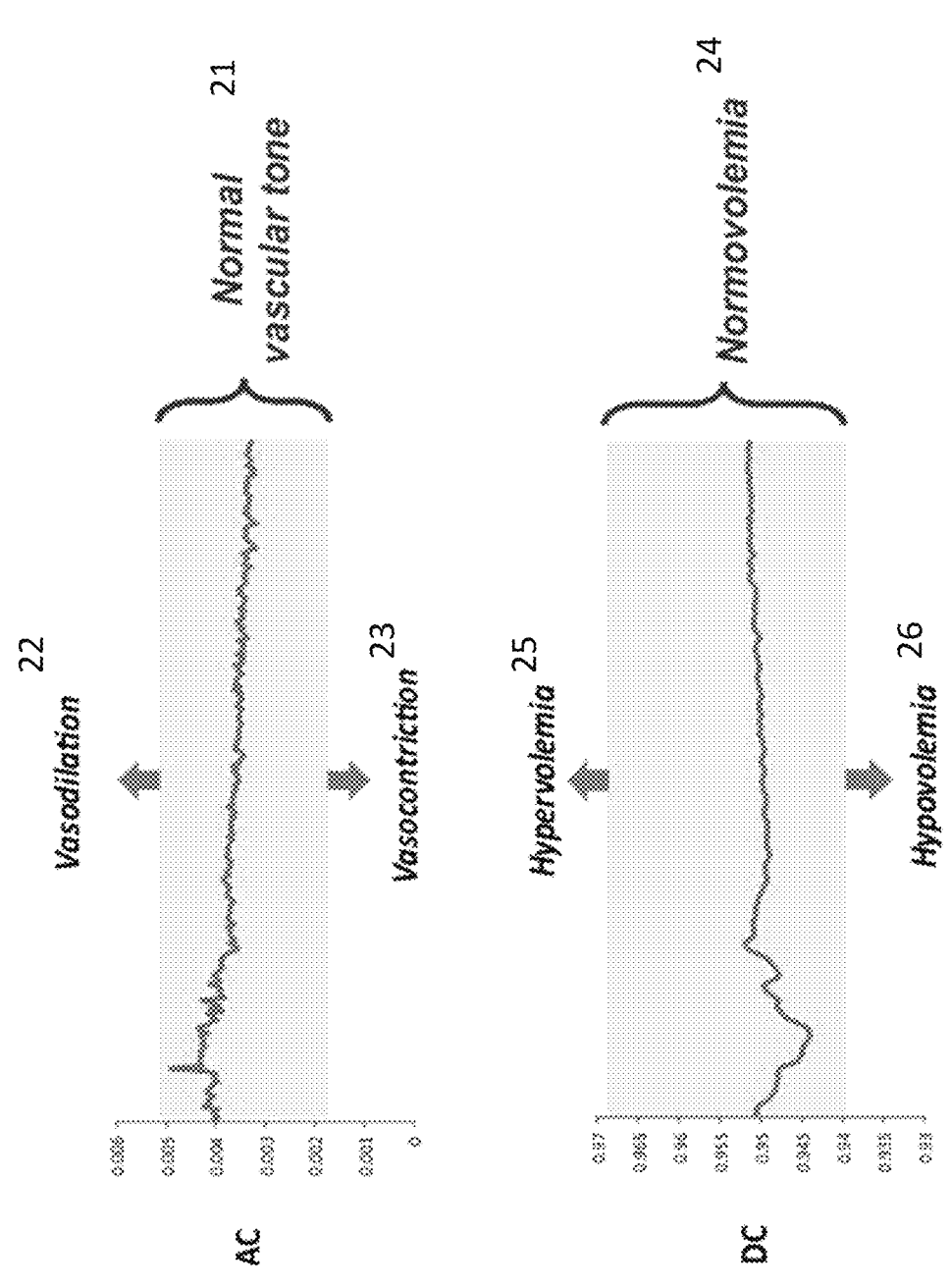
FIG. 8 shows a PPG measurement according to the invention for determining a volemia and/or determining a vasoconstriction or vasodilation using an apparatus according to the invention.

FIG. 8 shows a PPG measurement according to the invention for determining a volemia and/or determining a vasoconstriction or vasodilation using the apparatus according to the invention. A region of the AC signal which corresponds to the normal vascular tone 21 is defined for the AC signal 12 in the upper part of FIG. 8 by way of the calibration according to FIGS. 6,7.

If the AC signal deviates upwardly, this corresponds to a vasodilation 22.

If the AC signal deviates downwardly, this corresponds to a vasoconstriction 23.

The apparatus according to the invention and the method are configured and designed to receive a photoplethysmography (PPG) signal 11 by a computer 7, said signal comprising an alternating AC 12 component as PPG amplitude and the DC 13 component as PPG baseline from a sensor 2, 3, 9 in data communication with a living tissue 10;

determine a multiplicity of PPG signals from the living tissue by means of the computer 7;

determine a multiplicity of AC components 12 of the PPG signals by means of the computer 7, determine an AC signal trend over time by means of the computer 7 by comparing at least two AC components; and determine an AC signal trend over time which corresponds to a normal vascular tone and form a normal range 21 for AC values, identify AC signals which depart from the normal range 21 for AC values, determine a vasoconstriction 23 for AC signals which depart downwardly from the normal range 21 for AC values (in the direction of zero), determine a vasodilation 22 for AC signals which depart upwardly from the normal range 21 for AC values (in the direction of one).

The computer 7 is configured and designed to carry out the following method steps:

determining a multiplicity of PPG signals from the living tissue;

determining a multiplicity of AC components of the PPG signals, determining a multiplicity of DC components of the PPG signals, determining a multiplicity of AC waveforms from the AC components, and identifying differences in the AC waveforms over time by way of comparing at least two AC waveforms, determining a DC signal trend over time by comparing at least two DC components; and determining the volemic status and/or the vascular tone of the hemodynamic system of the living tissue as a reaction to at least one AC waveform difference and/or one DC signal trend over time.

For the DC signal 13 in the lower part of FIG. 8, a range of the DC signal that corresponds to a normal volemia 24 is defined by way of the calibration according to FIGS. 6,7.

If the DC signal deviates upwardly, this corresponds to a hypervolemia 25.

If the DC signal deviates downwardly, this corresponds to a hypovolemia 26.

The apparatus according to the invention and the method are configured and designed to receive a photoplethysmography (PPG) signal 11 by a computer 7, said signal comprising an alternating AC 12 component as PPG amplitude and the DC 13 component as PPG baseline from a sensor 2, 3, 9 in data communication with a living tissue 10;

determine a multiplicity of PPG signals from the living tissue by means of the computer 7;

determine a multiplicity of DC components 12 of the PPG signals by means of the computer 7, determine a DC signal trend over time by means of the computer 7 by comparing at least two DC components; and determine a DC signal trend over time which corresponds to a normal volemic status and form a normal range 24 for DC values, identify DC signals which depart from the normal range 24 for DC values, determine a hypervolemia 25 for DC signals which depart upwardly from the normal range 24 for DC values (in the direction of one), determine a hypovolemia 26 for DC signals which depart downwardly from the normal range 24 for DC values (in the direction of zero).

The apparatus according to the invention and the method are configured and designed to receive a photoplethysmography (PPG) signal 11 by a computer 7, said signal comprising an alternating AC 12 component as PPG amplitude and the DC 13 component as PPG baseline from a sensor 2, 3, 9 in data communication with a living tissue 10;

determine a multiplicity of PPG signals from the living tissue by means of the computer 7;

determine a multiplicity of AC components 12 of the PPG signals by means of the computer 7, determine a multiplicity of DC components 13 of the PPG signals by means of the computer 7, determine a multiplicity of AC waveforms from the AC components 12 by means of the computer 7, and identify differences in the AC waveforms over time by way of comparing at least two AC waveforms;

determine a DC signal trend over time by the computer 7 by way of comparing at least two DC components; and determine the volemic status 24, 25, 26 and/or the vascular tone 21, 22, 23 of the hemodynamic system of the living tissue 10 by means of the computer 7 as a reaction to at least one AC waveform difference and/or one DC signal trend over time.

What is claimed is:

1. A method for determining a volemic status and a vascular tone of the hemodynamic system, wherein the method comprises:

(i) sensory detection of a photoplethysmography (PPG) signal from a living tissue, the PPG signal having an alternating current (AC) component as a PPG amplitude and a direct current (DC) component as a PPG baseline, (ii) determining a multiplicity of PPG signals from the living tissue;

(iii) determining a multiplicity of AC components of the PPG signals, (iv) determining a multiplicity of DC components of the PPG signals, (v) determining a multiplicity of AC waveforms from the AC components, and (vi) identifying differences in the AC waveforms over time by comparing at least two of the AC waveforms, (vii) determining a DC signal trend over time by comparing at least two of the DC components; and (viii) determining the vascular tone and the volemic status of the hemodynamic system of the living tissue as a reaction to at least one of the AC waveform difference and/or the DC signal trend over time, respectively, and wherein a computer analyzes the AC components of the multiplicity of PPG signals as a measure for the vascular tone and determines a shift of the DC components of the multiplicity of PPG signals over time as a measure for the volemic status.

2. The method of claim 1, wherein
(i) to (v), (vii) and (viii) are carried out by the computer.

3. The method of claim 1, wherein the computer analyzes the multiplicity of PPG signals using a first or second derivative (d2DVP/dt2) of the PPG.

4. The method of claim 1, wherein the computer analyzes the multiplicity of PPG signals using artificial neural networks, an extraction of periodic components using frequency analyses or nonlinear dynamic analyses.

5. The method of claim 1, wherein a determination of a pulse frequency from one of the multiplicity of AC components comprises:

identifying a multiplicity of signal peaks within the one AC component by the computer;

identifying a time event for each of the multiplicity of signal peaks by the computer; and determining a multiplicity of time differences by the computer, each time difference being determined from a first time event of a first peak value of the multiplicity of signal peaks and a second time event of a second peak value of the multiplicity of signal peaks.

6. The method of claim 1, wherein a determination of a pulse strength metric comprises:

identifying a multiplicity of signal peaks within the multiplicity of AC components by the computer; and identifying an amplitude for each of the multiplicity of signal peaks by the computer.

7. The method of claim 6, wherein the method further comprises a determination of an average amplitude for at least some of the multiplicity of amplitudes by the computer.

8. The method of claim 1, wherein the computer analyzes a waveform of at least one of the multiplicity of AC components in order to identify at least one or more of a wave amplitude as a wave spacing from bottom to top, expressed in a scale from 0-100%, a systolic forward wave, a diastolic backward wave, a dichrotic notch which is determined by analysis of a first derivative of at least one of the multiplicity of PPG signals and which separates the systolic forward wave from the diastolic backward wave.

9. The method of claim 1, wherein the computer predicts the vascular tone of the hemodynamic system from a waveform of at least one of the multiplicity of AC components, a normal vascular tone being characterized by a waveform with a certain amplitude, with a dichrotic notch being located at between 15-50% of the wave amplitude.

10. The method of claim 1, wherein the computer uses a second PPG sensor in data communication with the living tissue, with the second PPG sensor being arranged at a different point in the living tissue in comparison with a first sensor in order to validate data from the first sensor; and/or the computer uses at least one other sensor and such sensor data in order to validate data from the first sensor; and/or the computer uses at least one other sensor and such sensor data in order to provide complementary information for a prediction of a state of the hemodynamic system.

11. The method of claim 1, wherein the computer is configured to verify a predicted volemia by virtue of including hemodynamic parameters from other sensors; and/or to verify a predicted vascular tone by virtue of including hemodynamic parameters from other sensors; and/or to carry out a PPG contour analysis which identifies wave amplitude and dichrotic notch position;

capturing changes in the multiplicity of DC components in relation to a baseline;

determining a specific hemodynamic condition on the basis of results of an analysis;

and calculating an amplitude and notch position and a shift of the multiplicity of DC components from the baseline for each pulse waveform; and/or to determine whether there is a relationship between the AC and the DC component of the PPG signal; and/or to calibrate the PPG signal by determining the multiplicity of PPG signals over time while the living tissue is arranged at heart level for a first time period, followed by a second time period, in which the living tissue is arranged above heart level, and followed by a third time period, in which the living tissue is arranged below heart level; and/or to calibrate the PPG signal by determining the multiplicity of PPG signals over time while the living tissue is arranged at heart level for a first time period following a second time period and/or a third time period; and/or to calibrate the PPG signal by determining the multiplicity of PPG signals over time, determining a multiplicity of AC components of the PPG signals and determining a multiplicity of DC components of the PPG signals while the living tissue is arranged level with a heart for a first time interval, followed by a second time interval in which the living tissue is arranged above heart level and followed by a third time interval in which the living tissue is arranged below heart level, wherein the computer stores values of PPG signals, including AC and DC components, from the first time interval, from the second time interval and the third time interval in order to determine a clinical range of normal values and highest-possible and lowest-possible limit values of the PPG signals, including AC and DC components, in relation to the vascular tone and the volemic status for a certain patient.

12. The method of claim 11, wherein the computer is configured to perform the calibration of the PPG signal by determining the multiplicity of PPG signals over time for the first period, followed by the second period and followed by the third period and stores values of PPG signals from the first time period as base values and values from the second time period as lower limit for vasodilation and/or hypovolemia and values from the third time period as upper limit for vasoconstriction and/or hypervolemia for a certain patient.

13. The method of claim 11, wherein the computer is configured to perform the calibration of the PPG signal by determining the multiplicity of PPG signals over time for the first period, followed by the second period and followed by the third period and the first, second and third time periods have the same length or wherein each of the first, second and third time periods takes as long as required to obtain a stable PPG signal.

14. The method of claim 1, wherein the computer is configured to apply a rule for alerting or warning medical staff on the basis of an actual prediction of the volemic status and/or the vascular tone of the hemodynamic system, the medical staff being alerted if the volemic status and/or the vascular tone increases or decreases by a predetermined relative or absolute value.

15. The method of claim 1, wherein the method is carried out during at least one obligatory respiratory cycle, with the computer being part of a medical ventilator or being connected to a medical ventilator in order to assess a cardiopulmonary interaction induced by the ventilator.

16. The method of claim 1, wherein the computer predicts the vascular tone of the hemodynamic system from a waveform of at least one of the multiplicity of AC components, with a vasoconstriction being characterized by a low waveform amplitude in relation to a normal PPG amplitude, a dichrotic notch being located at above 50% of the waveform amplitude.

17. The method of claim 1, wherein the computer predicts the vascular tone of the hemodynamic system from a waveform of at least one of the multiplicity of AC components, with a vasoconstriction being characterized by a low waveform amplitude without dichrotic notch or being merged into the systolic pulse wave(s).

18. The method of claim 1, wherein the computer predicts the vascular tone of the hemodynamic system from a waveform of at least one of the multiplicity of AC components, with a normal vasodilation being characterized by a high waveform amplitude with a dichrotic notch being below 15% of a waveform amplitude or even below zero.

19. The method of claim 1, wherein the computer predicts the volemic status of the hemodynamic system from the shift of the multiplicity of DC components over time, with hypervolemia being predicted if the shift of the multiplicity of DC components is beyond a defined baseline over time.

20. The method of claim 1, wherein the computer predicts the volemic status of the hemodynamic system from the shift of the multiplicity of DC components over time, with hypovolemia being predicted if there is a shift of the multiplicity of DC components is below a defined baseline over time.

* * * * *